United States Patent [19]

Yamamizu

[11] Patent Number: 4,791,183
[45] Date of Patent: Dec. 13, 1988

[54] STYRENE DERIVATIVE, POLYMER THEREOF AND PRODUCTION OF SAME

[75] Inventor: Takafumi Yamamizu, Kanagawa, Japan

[73] Assignee: Asahi Kasei Kogyo Kabushiki Kaisha, Osaka, Japan

[21] Appl. No.: 924,724

[22] Filed: Oct. 30, 1986

Related U.S. Application Data

[60] Division of Ser. No. 827,200, Feb. 7, 1986, abandoned, which is a continuation of Ser. No. 596,114, Apr. 2, 1984, abandoned.

[30] Foreign Application Priority Data

Apr. 1, 1983 [JP] Japan .................................. 58-55247
Apr. 4, 1983 [JP] Japan .................................. 58-58018
Apr. 4, 1983 [JP] Japan .................................. 58-59116
Apr. 4, 1983 [JP] Japan .................................. 58-59117

[51] Int. Cl.$^4$ ........................................... C08F 212/00
[52] U.S. Cl. ..................................... 526/261; 526/265; 526/286; 526/293
[58] Field of Search ................. 526/293, 261, 265, 286

[56] References Cited

U.S. PATENT DOCUMENTS 3,009,906  11/1961  Eichhorn et al. .................. 526/293
3,068,214  12/1962  Rassweiler et al. ................ 526/293
3,168,502  2/1965   Sexsmith et al. .................. 526/293
4,074,036  2/1978   Tuller et al. ..................... 526/293
4,262,081  4/1981   Bowden et al. .................... 526/293
4,361,684  11/1982  Minematsu et al. ................. 526/293

Primary Examiner—Joseph L. Schofer
Assistant Examiner—Bernard Lipman
Attorney, Agent, or Firm—Sughrue, Mion, Zinn, Macpeak, and Seas

[57] ABSTRACT

Disclosed herein is a new monomer as represented by the following formula (1):

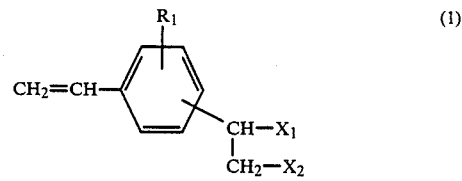

wherein $R_1$ is hydrogen or a $C_{1-10}$ hydrocarbon group, particularly a hydrogen atom, a methyl group or an ethyl group; and $X_1$ and $X_2$ are halogen atoms, particularly bromine atoms.

This new monomer is produced by reacting divinylbenzene or a substituted product thereof with a halogenating agent in which halogen molecules are inactivated, or halogen molecule under specific reaction conditions.

Also disclosed herein is a linear or crosslinked polymer produced from the monomer, as well as method of producing such polymers. The polymers are very useful in the preparation of functional polymers such as those having a chelating ability.

25 Claims, No Drawings

STYRENE DERIVATIVE, POLYMER THEREOF AND PRODUCTION OF SAME

This is a division of application Ser. No. 827,200, filed 2/7/86, now abandoned, which is a continuation of application Ser. No. 596,114, filed 4/2/84, now abandoned.

FIELD OF THE INVENTION

The present invention relates to a new monomer and polymer thereof and a process for producing the same. More particularly, it relates to a new styrene derivative and a polymer thereof and a process for producing the same.

BACKGROUND OF THE INVENTION

Heretofore, there have been developed a variety of styrene derivatives for synthesis of functional polymers. For example, cyanostyrene and aminostyrene are easily made into polymers having various functional groups by radical polymerization.

On the other hand, there are known chlorostyrene, bromostyrene, chloromethylstyrene, and p-(2-bromoethyl)styrene as the styrene derivative having a halogen atom. Also, there is known bis-(1,2-dihalogenoethyl)-benzene formed by attaching four halogen atoms to the two vinyl groups of divinylbenzene.

SUMMARY OF THE INVENTION

The present inventors have now developed a 1,2-dihalogenoethyl styrene having both a vinyl group and 1,2-dihalogenoethyl group.

The present inventors carried out a series of experiments on the reaction of divinylbenzene or a derivative thereof with a halogenating agent. As the result, they succeeded in the synthesis and separation of a new monomer as represented by the following formula (1):

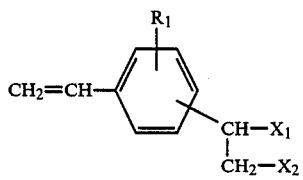

wherein $R_1$ is a hydrogen atom or a $C_{1-10}$ hydrocarbon group; and $X_1$ and $X_2$ are halogens.

A primary object of this invention is to provide a new monomer represented by the formula (1):

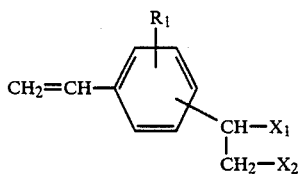

wherein $R_1$ is a hydrogen atom or a $C_{1-10}$ hydrocarbon group; and $X_1$ and $X_2$ are halogens.

Another object of this invention is to provide a polymer or copolymer made from monomer (1).

Still another object of this invention is to provide a process for producing the monomer (1).

A still further object of this invention is to provide a process for producing a polymer of the monomer (1).

DETAILED DESCRIPTION OF THE INVENTION

In formula (1), $R_1$ preferably represents a hydrogen atom, a $C_{1-10}$ alkyl group, an aryl group and an aralkyl group, more preferably a hydrogen atom, a methyl group and an ethyl group. $X_1$ and $X_2$ are preferably a chlorine atom, a bromine atom, or an iodine atom, and they may be the same or different from one another.

The 1,2-dihalogenoethyl group is preferably at the meta position or para position with respect to the vinyl group.

The 1,2-dihalogenoethylstyrene and a substituted product thereof of this invention is produced by reacting divinylbenzene or a substituted product thereof with halogen molecules or halogenating agent in which halogen molecules are inactivated.

The divinylbenzene is preferably m-divinylbenzene or p-divinylbenzene or a mixture of both. It is also possible to use substituted divinylbenzene having a $C_{1-10}$ alkyl group, an aryl group, an aralkyl group, or other hydrocarbon group; or to use commercial divinylbenzene.

The halogenation can be accomplished with halogen molecules such as chlorine, bromine, and iodine; however, for better control of reaction rate and selectivity, it is preferable to use a halogenating agent in which the halogen molecules are inactivated. Where halogen molecules are directly used, attention should be paid to the temperature and the rate and quantity of addition as described later. Examples of a halogenating agent in which halogen molecules are inactivated include an addition product of an iodized aromatic compound and halogen molecules such as iodobenzenedibromide

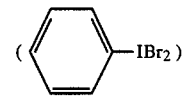

and an addition product of a nitrogen compound and halogen molecules. A preferred one is an addition product of halogen molecules and a nitrogen compound or hydrogen halide salt of nitrogen compound. More preferred examples of such addition products are pyridiniumhydrobromide perbromide

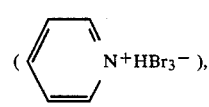

tetramethylammoniumbromide perbromide $((CH_3)_4N^+Br_3^-)$, tetramethylammoniumbromide perchloride $((CH_3)_4N^+BrCl_2^-)$, phenyltrimethylammoniumbromide perbromide

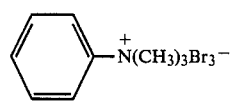

and 2,4-diamino-1,3-thiazolehydrotribromide

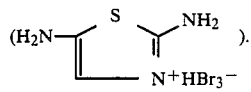

The halogenating agent is used in an amount of 0.1 to 2.0 mol, preferably 0.4 to 0.9 mol per mol of divinylbenzene. When halogen molecules are used as the halogenating agent, the amount is preferably 0.1 to 0.8 mol per mol of divinylbenzene. Further, the halogen molecules are preferably added as slowly as 1 g/min. or lower per 100 g of divinylbenzene.

This reaction may be accomplished in the presence of an inert fluid which is not halogenated and does not interfere with the addition of halogen to divnylbenzene. Preferred examples of such as inert fluid include pentane, hexane, heptane, and other aliphatic hydrocarbons; methanol, ethanol, isopropyl alcohol, and other alcohols; benzene, toluene, xylene, and other aromatic hydrocarbons; ethyl acetate, ethyl benzoate, and other esters; dimethyl formamide, dimethyl acetamide, and other amides; chloroform, methylene chloride, tetrachloroethylene, and other halogenated hydrocarbons; acetone, methyl ethyl ketone, diethyl ketone, and other ketones; diethyl ether, methyl ethyl ether, dioxane, and other ethers; acetic acid, propionic acid and other carboxylic acid. Of these, aliphatic hydrocarbons such as hexane and heptane; halogenated hydrocarbons such as methylene chloride and carbon tetrachloride; carboxylic acids such as acetic acid and propionic acid; and alcohols such as methanol and ethanol are particularly preferred. They are used individually or in combination with one another.

The reaction temperature is $-100°$ C. to $100°$ C., depending on the type of halogenating agent used. It should preferably be $-50°$ C. to $30°$ C. where an inactivated halogenating agent is used. It should be $-20°$ C. to $10°$ C. where the reaction is to be performed selectively and efficiently. It is preferably $-70°$ C. to $0°$ C., more preferably $-70°$ C. to $-30°$ C., where halogen molecules are used directly as the halogenating agent.

When halogen molecules are added to divinylbenzene under the conventional condition, there is obtained almost quantitatively bis-(1,2-dihalogenoethyl)benzene in which the halogen molecules are attached to both vinyl groups. The present inventors found that the addition reaction yields not only bis-(1,2-dihalogenoethyl)-benzene but also 1,2-dihalogenoethylstyrene if the reaction conditions are properly varied.

The reaction time is not specifically limited; but it should properly be selected according to the reaction rate which varies depending on the type of inert fluid and kind and addition rate of halogenating agent used. The proper reaction time may be established by determining the quantity of the reaction product by gas chromatography from time to time.

The recommended reaction method is described below: place in a flask an inert fluid in which divinylbenzene has been dissolved. Sufficiently cool the flask while stirring. Add a halogenating agent little by little, taking care that the temperature does not rise. Trace the reaction by means of gas chromatography. After confirming that the reaction has terminated, stop the reaction. Separate the reaction product from the reaction mixture and purify it by extraction or distillation or other ordinary methods.

The monomer (1) of this invention can be easily made into a polymer by homopolymerization or copolymerization with other monomers. The resulting polymer has as side chains 1,2-dihalogenoethylphenyl groups which can be changed into various functional groups by proper reactions. Polymers having such functional groups are very useful. For example, a polymer having an anion exchange ability is formed when the side chain is reacted with a nitrogen compound. Also, a polymer having a chelating ability is formed when an iminodiacetic acid group

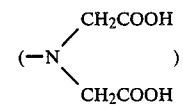

is introduced into the side chain. A similar polymer can be produced from an alkyl-substituted styrene having a halogen atom such as p-(2-bromoethyl)styrene and chloromethylstyrene. Such a polymer, however, is quite different from the one produced from the above-mentioned monomer. This difference is apparent in the case of chelating polymer formed by introducing an iminodiacetic acid group. When an iminodiacetic acid group is introduced into a polymer formed from 1,2-dihalogenoethylstyrene, there is formed a side chain in which two iminodiacetic acid groups are arranged side by side as shown in the following structural formula (A).

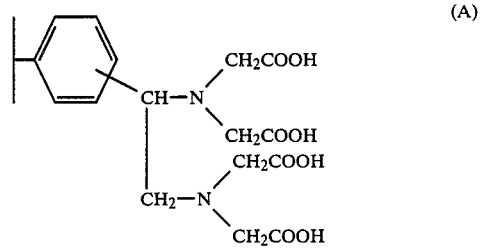

(A)

In contrast, the side chain formed by introducing an iminodiacetic acid group into a polymer formed from chloromethylstyrene has the following structural formula (B).

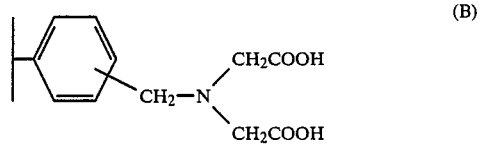

(B)

The side chain of (A) has a greater chelating ability than the side chain of (B). Thus it is understood that the chelating polymer formed from 1,2-dihalogenoethylstyrene is very useful as a metal removing agent.

Moreover, the polymer formed from 1,2-dihalogenoethylstyrene is useful as a flame retarding polymer because it contains two halogen atoms in the side chain.

As described above, the monomer (1) of the present invention provides useful polymers by homopolymerization or copolymerization with other comonomers.

An embodiment of polymers of the present invention is a linear polymer having a molecular weight of 1,000 to 1,000,000, more preferably 10,000 to 1,000,000 and having the following repeating unit (2):

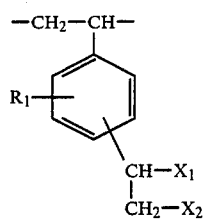 (2)

where $R_1$, $X_1$ and $X_2$ each has the same meanings as defined above. The 1,2-dihalogenoethyl group is preferably positioned at the meta or para position or its mixture with respect to the main chain. The polymer can be prepared by the polymerization of the monomer (1).

A further embodiment of polymers of the present invention is a crosslinked copolymer having 10 to 98 mol% of the repeating unit (2), 2 to 50 mol% of the following repeating unit(s) (3) and/or (4) and 0 to 80 mol% of the following repeating unit (5);

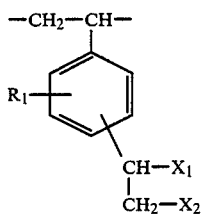 (2)

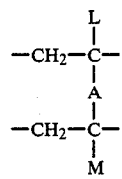 (3)

(4)

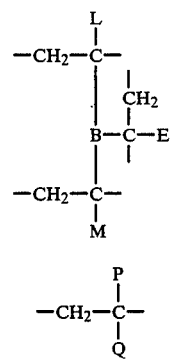

(5)

where $R_1$, $X_1$ and $X_2$ each has the same meaning as defined above; L, M and E each represents a hydrogen atom or a methyl group; A is a divalent group selected from (i)

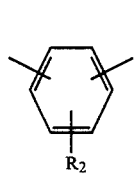

(wherein $R_2$ is hydrogen atom or a $C_{1-5}$ hydrocarbon group), (ii)

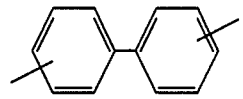

(iii)

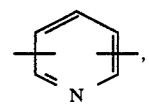

(wherein D represents —O—, —S—, —NH— or a $C_{1-5}$ alkylene group), (iv) —SO—, —CO— or

(v) —CH$_2$—NH—CH$_2$—, (vi)

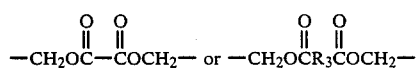

(wherein $R_3$ is a divalent $C_{1-8}$ hydrocarbon group), (vii)

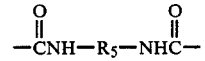

(wherein $R_4$ is a divalent $C_{1-5}$ hydrocarbon group), and (viii)

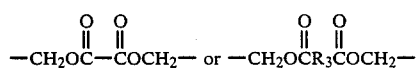

(wherein $R_5$ is a divalent $C_{1-3}$ hydrocarbon group); B is a trivalent group selected from (i)

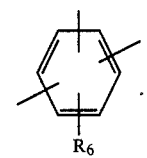

(wherein $R_6$ is a hydrogen atom or a $C_{1-5}$ hydrocarbon group), (ii)

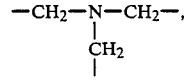

and (iii)

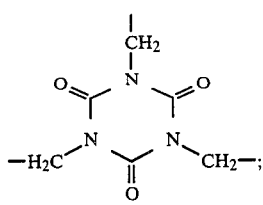

and P and Q each represents a hydrogen atom, a halogen atom, a $C_{1-10}$ alkyl or haloalkyl group, a cyano group, an aryl group, a halogenophenyl group, a hydroxyphenyl group, a hydroxymethylphenyl group, a carboxyphenyl group, an alkylphenyl group having a $C_{1-5}$ alkyl moiety, a haloalkylphenyl group, a hydroxyalkylphenyl group, a hydroxymethylalkylphenyl group, a carboxyalkylphenyl group, $-COOR_7$ (wherein $R_7$ is a hydrogen atom or a $C_{1-10}$ hydrocarbon group), $-COR_8$ (wherein $R_8$ is a hydrogen atom or a $C_{1-10}$ hydrocarbon group), $-OCOR_9$ (wherein $R_9$ is a $C_{1-10}$ hydrocarbon group) and $-CONHR_{10}$ (wherein $R_{10}$ is a hydrogen atom or a $C_{1-10}$ hydrocarbon group).

In the crosslinked copolymers, L, M and N are preferably a hydrogen atom; A is preferably

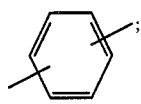

B is preferably

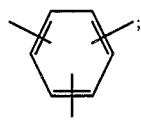

and P and/or Q is preferably a hydrogen atom.

The crosslinked copolymer can be prepared by the copolymerization of the monomer (1) and monomers of the following formula(s) (6) and/or (7), optionally with a monomer of the following formula (8).

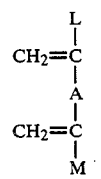

(6)

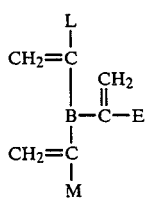

(7)

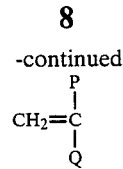

(8)

Examples of the monomers (6) and (7) include divinylbenzene, divinyltoluene, divinylxylene, divinyllethylbenzene, trivinylbenzene, divinyldiphenyl, divinyldiphenylmethane, divinyldibenzyl, divinylphenyl ether, divinyldiphenylsulfide, divinyldiphenylamine, divinylsulfone, divinyl ketone, divinylpyridine, diallyl phthalate, diallyl maleate, diallyl fumarate, diallyl succinate, diallyl oxalate, diallyl adipate, diallyl sebacate, diallylamine, triallylamine, N,N'-ethylenediacrylamide, N,N'-methylenediacrylamide, N,N'-methylenedimethacrylamide, ethylene glycol dimethacrylate, ethylene glycol diacrylate, 1,3-butylene glycol diacrylate, triallyl isocyanurate, triallyl citrate, triallyl trimellitate and triallyl cyanurate. These monomers may be used alone or as a mixture thereof.

Examples of the monomer (8) include styrene derivatives such as styrene, methylstyrene, diphenylethylene, ethylstyrene, dimethylstyrene, vinylbenzoic acid, vinylbenzyl alcohol, vinylphenol, ethylvinylbenzoic acid, ethylvinylbenzyl alcohol, chlorostyrene, methoxystyrene, bromostyrene, cyanostyrene, fluorostyrene, dichlorostyrene, chloromethylstyrene, trifluorostyrene and trifluoromethylstyrene; hydrocarbon compounds such as vinylnaphthalene, vinylphenanthrene, vinylmesitylene and 3,4,6-trimethylstyrene; acrylonitrile derivatives such as acrylonitrile, methacrylonitrile and α-acetoxyacrylonitrile; acrylic or methacrylic acid; acrylates such as methyl acrylate, lauryl acrylate, chloromethyl acrylate and ethyl acetoxyacrylate; methacrylates such as cyclohexyl methacrylate, dimethylaminoethyl methacrylate, glicidyl methacrylate, tetrahydrofurfuryl methacrylate and hydroxyethyl methacrylate; diethyl maleate; diethyl fumarate; vinyl ketones such as methyl vinyl ketone and ethyl isopropenyl ketone; vinylidene compounds such as vinylidene chloride, vinylidene bromide and vinylidene cyanide; acrylamide derivatives such as acrylamide, methacrylamide, N-butoxymethylacrylamide and N-phenylacrylamide; and aliphatic acid vinyl ester derivatives such as vinyl acetate, vinyl butyrate and vinyl caprate.

In this embodiment, other unsaturated monomers may also be copolymerized, for example, hydrocarbon compounds such as 1-vinyl-2-ethylacetylene, butadiene, isoprene and piperylene; styrene derivatives such as N,N-dimethylaminostyrene, nitrostyrene and aminostyrene; vinyl sulfide derivatives such as methylvinylsulfide and phenylvinylsulfide; acrylamide derivatives such as diacetoneacrylamide and N,N-dimethylaminoethylacrylamide; thioaliphatic acid derivatives such as phenyl thiomethacrylate, methyl thioacrylate and vinyl thioacetate; and heterocyclic vinyl compounds such as N-vinylsuccinimide, N-vinylpyrrolidone, N-vinylphthalimide, N-vinylcarbazole, vinylfuran, 2-vinylbenzofuran, vinylthiophene, vinylimidazole, methylvinylimidazole, vinylpyrazole, vinyloxazolidone, vinylthiazole, vinyltetrazole, vinylpyridine, methylvinylpyridine, 2,4-dimethyl-6-vinyltriazine and vinylquinoline.

Another embodiment of polymers of the present invention is a linear copolymer having a molecular weight of 1,000 to 2,000,000, preferably 10,000 to 2,000,000 and having the repeating units (2) and (5):

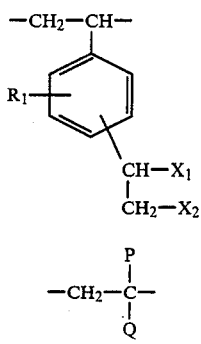

wherein $R_1$, $X_1$, $X_2$, P and Q each has the same meanings as defined above. In the copolymer, P and Q preferably represent a hydrogen atom, a chlorine atom, a cyano group, a methyl group, a phenyl group, a chlorophenyl group, —COOH, —COOCH$_3$, —COOC$_6$H$_{11}$, —COCH$_3$, —OCOCH$_3$ and —CONH$_2$, with an hydrogen atom being more preferred for one of P and Q. The repeating unit (5) in the copolymer may be the same or different.

There is no particular limitation on the mol fractions of the repeating units in the linear copolymer, but the repeating unit (2) is generally included in an amount of 10 to 98 mol% and preferably 20 to 80 mol%. Further, another repeating unit may be included in the copolymer to an extent that the properties of copolymer is not substantially changed. The linear copolymer can be prepared by the copolymerization of the monomers (1) and (8) as described above.

With respect to the polymerization or copolymerization conditions there is no limitation, and conventional methods can be employed. While the polymerization can be carried out merely by heating, in many cases a polymerization initiator is advantageously used. Examples of polymerization initiator include acyl peroxides such as benzoyl peroxide and lauroyl peroxide, azonitriles such as azobisisobutyronitrile and 2,2′-azobis(2,4-dimethylvaleronitrile), peroxides such as di-t-butyl peroxide, dicumyl peroxide and methyl ethyl ketone peroxide, and hydroperoxides such as cumene hydroperoxide and t-butyl hydroperoxide.

The polymers of the present invention can also be produced by the polymerization in the presence of inert fluid. Examples of inert fluid include aliphatic hydrocarbons such as n-pentane, n-hexane, n-heptane and n-octane, alcohols such as methanol, ethanol and isopropyl alcohol, ketones such as acetone, methyl ethyl ketone and diethyl ketone, ethers such as diethyl ether, methyl ethyl ether, dibutyl ether, dioxane and tetrahydrofuran, aromatic hydrocarbons such as benzene, toluene and xylene, esters such as ethyl formate, ethyl acetate and butyl acetate, amides such as dimethylformamide and dimethylacetamide, aliphatic halides such as chloroform, methylene chloride and dichloroethane, aromatic halides such as chlorobenzene, and polar liquid such as dimethylsulfoxide. These may be used alone or as a mixture thereof.

The polymerization temperature is not limited, but generally from 20° to 120° C., preferably from 60° to 100° C.

The invention is now described in more detail with reference to the following non-limitative examples.

EXAMPLE 1

Into a 2-liter four-neck flask equipped with a thermometer, reflux condenser, and stirrer were charged 1 liter of methylene chloride and 130.0 g (1.0 mol) of m-divinylbenzene. While the temperature was kept at −5° C. with stirring, 255.5 8 g (0.8 mol) of pyridiniumhydrobromide perbromide was added in ten 25-g portions. Stirring was continued for about 2 hours at the same temperature. One liter of 1N hydrochloric acid was added to the reaction product, and pyridiumhydrobromide was removed. The reaction product was washed twice with 500 ml of pure water. Methylene chloride was distilled away by using an evaporator, and the reaction product underwent distillation under reduced pressure. The temperature was gradually raised while the pressure in the evaporator was kept at 1 mmHg. At 33° C., unreacted m-divinylbenzene was distilled away. Then, at 101° C., a pale yellow liquid was distilled away. The yield of this liquid was 204.7 g (71%). This liquid was found to be a simple substance by gas chromatography and liwuid chromatography. The simple substance was identified to be 3-(1,2-dibromoethyl)styrene by spectral analyses and other chemical analyses. The results of the analyses are as follows:

Elemental analysis: C: 41.13 (41.42), H: 3.65 (3.48), Br: 55.22 (55.11). (Calculated values are shown in parentheses.)

Mass spectrum: 292 (P+4), 290 (P+2), 288 (M+/e), 261 (M—C$_2$H$_3$), 103 (M—C$_2$H$_3$Br$_2$), 76 (C$_6$H$_4$).

Infrared absorption spectrum: 3020, 2970, 1630, 1510, 1480, 1215, 1155, 980, 910, 800 cm$^{-1}$.

Proton NMR spectrum: (60 MHz; solvent: deuterochloroform; reference material: tetramethylsilane) δvalue: 3.97 (doublet, 2H), 4.9–5.4 (multiplet, 2H), 5.73 (doublet doublets, 1H), 6.67 (double doublets, 1H), 7.0–7.7 (multiplet, 4H).

EXAMPLE 2

Into a 1-liter four-neck flask equipped with a thermometer, reflux condenser, and stirrer were charged 500 ml of methylene chloride and 65.0 g (0.5 mol) of p-divinylbenzene. While the temperature was kept at −10° C. with stirring, 125.6 g (0.4 mol) of tetramethylammoniumbromide perbromide was added in fifteen 8-g portions. Stirring was continued for about 2 hours at the same temperature. 500 ml of 1N hydrochloric acid was added to the reaction product, and tetramethylammonium bromide was removed. The reaction product was washed twice with 250 ml of pure water. Methylene chloride was removed by using an evaporator and the reaction product underwent distillation under reduced pressure. The temperature was gradually raised while the pressure in the evaporator was kept at 1 mmHg. At 42° C., unreacted p-divinylbenzene was distilled away. Then, the temperature was raised to 200° C., but no distillate was obtained. On cooling to room temperature, the residual liquid became a white solid. The melting point of this solid was 107° to 110° C., and the yield of this solid was 92.4 g (64%). This solid was found to be a simple substance by gas chromatography and liquid chromatography. The simple substance was identified to be 4-(1,2-dibromoethyl)styrene by spectral analyses and other chemical analyses. The results of the analyses are as follows:

Elemental analysis: C: 41.21 (41.42), H: 3.40 (3.48), Br: 55.18 (55.11). (Calculated values are shown in parentheses.)

Mass spectrum: 292 (P+4), 290 (P+2), 288 (M+/e), 261 (M—C$_2$H$_3$), 103 (M—C$_2$H$_3$Br$_2$), 76 (C$_6$H$_4$).

Infrared absorption spectrum: 3020, 2910, 1625, 1600, 1510, 1430, 1130, 985, 910, 835 cm$^{-1}$.

Proton NMR spectrum: (60 MHz; solvent: deuterochloroform; reference material: tetramethylsilane) δvalue: 3.97 (doublet, 2H), 4.9–5.4 (multiplet, 2H), 5.73 (double doublets, 1H), 6.67 (double doublets, 1H), 7.0–7.6 (multiplet, 4H).

EXAMPLE 3

Into a 1-liter four-neck flask equipped with a thermometer, reflux condenser, and stirrer were charged 500 ml of methylene chloride and 65.0 g (0.5 mol) of m-divinylbenzene. While the temperature was kept at −40° C. with stirring, 63.9 g (0.4 mol) of bromine was added at a rate of about 1 g per minute by using an dropping funnel. Stirring was continued for about 1 hour at the same temperature. Methylene chloride was distilled away by using an evaporator, and the reaction product was treated as in Example 1. Thus there was obtained 21.8 g (15%) of reaction product. This reaction product gave the same analytical results as those of the reaction product in Example 1. Thus it was identified to be 3-(1,2-dibromoethyl)styrene.

EXAMPLE 4

Into a 20-ml ampoule were charged 5.0 g of 3-(1,2-dibromoethyl)styrene, 5 ml of m-xylene, and 0.05 g of azobisisobutyronitrile. After complete mixing and dissolution, the air in the ampoule was replaced with nitrogen, and the ampoule was sealed. The ampoule was dipped in water at 90° C. for 24 hours. After cooling, the ampoule was broken and the content was placed in hexane. The resulting precipitates were filtered off and washed thoroughly with hexane. The weight of the precipitates measured after vacuum-drying was 4.9 g. This reaction product gave the following results of elemental analysis and the peaks in the infrared absorption spectrum.

Elemental analysis: C: 41.38 (41.42), H: 3.42 (3.48), Br: 55.20 (55.11). (Calculated values are shown in parentheses.)

Infrared absorption spectrum: 3020, 2970, 1600, 1510, 1480, 1215, 800, 690 cm$^{-1}$.

The fact that the absorption due to the C═C double bond in the monomer disappeared indicated that the reaction product is a polymer. The molecular weight of this polymer was 110,000 when measured by gel permeation chromatography that employs polystyrene for the calibration curve.

EXAMPLE 5

Example 4 was repeated, except that 3-(1,2-dibromoethyl)styrene was replaced by 4-(1,2-dibromoethyl)styrene. The yield was 4.8 g. The reaction product gave the following results of elemental analysis and the peaks in the infrared absorption spectrum.

Elemental analysis: C: 41.35 (41.42), H: 3.39 (3.48), Br: 55.26 (55.11). (Calculated values are shown in parentheses.)

Infrared absorption spectrum: 3020, 2910, 1600, 1510, 1430, 1230, 835, 695 cm$^{-1}$.

The molecular weight measured in the same way as in Example 4 was 90,000.

EXAMPLE 6

Into a 30-ml ampoule were charged 8.70 g of 3-(1,2-dibromoethyl)styrene, 3.13 g of styrene, and 0.15 g of azobisisobutyronitrile. After complete mixing and dissolution, the air in the ampoule was replaced with nitrogen, and the ampoule was sealed. The ampoule was dipped in water at 90° C. for 24 hours. The solid content was taken out by breaking the ampoule. The weight of the solid measured after methanol washing and vacuum drying was 11.72 g (yield 99%). This reaction product gave the following results of elemental analysis and the peaks of the infrared absorption spectrum.

Elemental analysis: C: 53.35 (53.43), H: 4.90 (4.75), Br: 41.75 (41.82). (Calculated values are shown in parentheses.)

Infrared absorption spectrum: 3020, 2970, 1600, 1510, 1480, 1215, 800, 690 cm$^{-1}$.

The fact that the peak due to the C═C double bond disappeared indicates that the reaction product is a copolymer of 3-(1,2-dibromoethyl)styrene and styrene. This was also supported by the results of elemental analysis and the yield.

The molecular weight of this polymer was 200,000 when measured by gel permeation chromatography that employs polystyrene for the calibration curve.

EXAMPLE 7

Example 6 was repeated, except that 3-(1,2-dibromoethyl)styrene was replaced by 4-(1,2-dibromoethyl)styrene. The yield was 11.60 g (yield 98%). The reaction product gave the following results of elemental analysis and the peaks in the infrared absorption spectrum.

Elemental analysis: C: 53.37 (53.43), H: 4.87 (4.75), Br: 41.76 (41.82). (Calculated values are shown in parentheses.)

Infrared absorption spectrum: 3020, 2910, 1600, 1510, 1430, 1230, 835, 695 cm$^{-1}$.

The molecular weight of the reaction product was 150,000 when measured in the same way as in Example 4.

EXAMPLES 8 TO 16

A monomer of formula (1) and a monomer of formula (8) (defined above) were copolymerized in the same way as in Example 6. The resulting copolymer underwent elemental analysis and infrared absorption spectrometry. The results are shown in Table 1.

TABLE 1

| Example | Compound of formula (1) Name | (g) | Compound of formula (8) Name | (g) | Initiator | Inert fluid | Polymerization conditions Temp. (°C.) × time (hour) | Molecular weight (× 10$^3$) | Yield (%) |
|---|---|---|---|---|---|---|---|---|---|
| 8 | 3-(1,2-dibromoethyl)styrene | 8.70 | Vinyl acetate | 2.58 | AIBN 0.11 g | Methyl ethyl ketone | 70 × 8 | 120 | 98 |
| 9 | 3-(1,2-dibromoethyl)styrene | 8.70 | Acrylonitrile | 1.59 | AIBN 0.10 g | None | 70 × 8 | 110 | 97 |
| 10 | 4-(1,2-dibromo- | 8.70 | Vinylidene | 2.91 | AIBN | None | 80 × 5 | 50 | 95 |

TABLE 1-continued

| | | | | | | | | | |
|---|---|---|---|---|---|---|---|---|---|
| | ethyl)styrene | | chloride | | | | 0.12 g | | |
| 11 | 4-(1,2-dibromo-ethyl)styrene | 8.70 | Methyl methacrylate | 3.00 | AIBN 0.12 g | Methyl ethyl ketone | 80 × 5 | 60 | 99 |
| 12 | 4-(1,2-dibromo-ethyl)styrene | 8.70 | Acrylamide | 2.13 | AIBN 0.11 g | None | 80 × 5 | 100 | 99 |
| 13 | 3-(1,2-dibromo-ethyl)styrene | 8.70 | Methacrylic acid | 2.58 | AIBN 0.11 g | Methyl ethyl ketone | 80 × 5 | 40 | 95 |
| 14 | 3-(1,2-dibromo-ethyl)styrene | 8.70 | Methyl vinyl ketone | 2.10 | AIBN 0.11 g | None | 70 × 8 | 40 | 93 |
| 15 | 3-(1,2-dibromo-ethyl)styrene | 8.70 | Chloromethyl styrene (m/p = 6/4) | 4.58 | AIBN 0.13 g | Toluene | 80 × 5 | 250 | 99 |
| 16 | 3-(1,2-dibromo-ethyl)styrene | 8.70 | Cyclohexyl methacrylate | 5.05 | AIBN 0.14 g | Octane | 80 × 5 | 90 | 92 |

| Example | Elemental analysis (%) (calculated values in parentheses) | Main peaks in infrared spectrum (cm$^{-1}$) |
|---|---|---|
| 8 | C: 44.67 (44.71), H: 4.32 (4.29), O: 8.53 (8.51), Br: 42.48 (42.49). | 690, 800, 1215, 1480, 1510, 1600, 1750, 2970, 3020. |
| 9 | C: 45.54 (45.51), H: 3.84 (3.82), N: 4.09 (4.08), Br: 46.53 (46.58). | 690, 800, 1215, 1480, 1510, 1600, 2230, 2970, 3020. |
| 10 | C: 37.21 (37.25), H: 3.16 (3.13), Cl: 18.36 (18.32), Br: 41.27 (41.30). | 680, 835, 1230, 1430, 1510, 1600, 2910, 3020. |
| 11 | C: 46.20 (46.18), H: 4.70 (4.65), O: 8.15 (8.20), Br: 40.95 (40.96). | 695, 835, 1230, 1430, 1510, 1600, 1730, 2910, 3020. |
| 12 | C: 43.51 (43.49), H: 371 (3.65), N: 3.86 (3.90), O: 4.51 (4.46), Br: 44.41 (44.51). | 695, 835, 1230, 1430, 1510, 1600, 1640, 2910, 3020. |
| 13 | C: 44.63 (44.71), H: 4.35 (4.29), O: 8.47 (8.51), Br: 42.55 (42.49). | 690, 800, 1215, 1480, 1510, 1600, 1710, 2970, 3020. |
| 14 | C: 46.72 (46.70), H: 4.51 (4.48), O: 4.32 (4.44), Br: 44.45 (44.38). | 690, 800, 1215, 1480, 1510, 1600, 1715, 2970, 3020. |
| 15 | C: 51.51 (51.56), H: 4.38 (4.33), Cl: 8.07 (8.01), Br: 36.04 (36.11). | 690, 800, 1215, 1270, 1480, 1510, 1600, 2970, 3020. |
| 16 | C: 52.38 (52.42), H: 5.66 (5.72), O: 7.05 (6.98), Br: 34.91 (34.87). | 690, 800, 1215, 1480, 1510, 1600, 1730, 2970, 3020. |

EXAMPLE 17

Into a 50-ml ampoule were charged 11.60 g of 3-(1,2-dibromoethyl)styrene, 4.65 g of divinylbenzene (purity 56%, m/p=7/3, containing 44% of ethylstyrene), and 10 ml of toluene. After mixing, 0.14 g of azobisisobutyronitrile was added. After complete mixing, the air in the ampoule was replaced with nitrogen, and the ampoule was sealed. The ampoule was dipped in water at 90° C. for 8 hours to bring about reaction. After cooling, the ampoule was broken and the content was taken out, followed by washing with acetone and vacuum drying. The yield of the polymer was 16.12 g. The result of elemental analysis is given below.

C: 55.75 (55.79), H: 4.83 (4.87), Br: 39.42 (39.42). (Calculated values are shown in parentheses.)

The main peaks in the infrared absorption spectrum are as follows:

3020, 2970, 1600, 1510, 1480, 1215, 800, 690 cm$^{-1}$.

The fact that the resulting solid is completely insoluble in acetone, the yield is 99.2%, and the absorption due to the C=C couble bond in the monomer disappeared indicates that the reaction product was a copolymer of 3-(1,2-dibromoethyl)styrene, divinylbenzene, and ethylstyrene.

EXAMPLES 18 TO 30

Experiments were carried out in the same way as in Example 17. The results are shown in Table 2.

TABLE 2

| Example | Compound | (g) | Compound | (g) | Compound | (g) | Compound | (g) | Initiator | Inert fluid | Temp. (°C.) × time (h) | Yield (%) | Elemental analysis |
|---|---|---|---|---|---|---|---|---|---|---|---|---|---|
| 18 | 3-(1,2-dibromoethyl)styrene | 8.70 | — | | Triallylisocyanurate | 4.99 | — | | AIBN 0.14 | Methanol 10 ml | 90 × 8 | 98 | C: 47.43 (47.40) H: 4.45 (4.42) N: 6.10 (6.14) O: 7.10 (7.01) Br: 34.92 (35.03) |
| 19 | 3-(1,2-dibromoethyl)styrene | 8.70 | m-Divinylbenzene | 2.60 | — | | Ethylstyrene | 1.32 | AIBN 0.13 | Toluene 10 | 90 × 8 | 99 | C: 57.15 (57.08) H: 4.91 (4.95) Br: 37.94 (37.97) |
| 20 | 3-(1,2-dibromoethyl)styrene | 8.70 | 4,4'-Divinylbiphenyl | 4.13 | — | | Styrene | 1.04 | AIBN 0.14 | Toluene 10 | 90 × 8 | 96 | C: 60.68 (60.63) H: 4.72 (4.80) Br: 34.60 (34.57) |
| 21 | 3-(1,2-dibromoethyl)styrene | 8.70 | Di(p-vinylphenyl)methane | 4.41 | — | | — | | AIBN 0.13 | Toluene 10 | 90 × 8 | 97 | C: 58.61 (58.65) H: 4.79 (4.77) Br: 36.60 (36.58) |
| 22 | 3-(1,2-dibromoethyl)styrene | 8.70 | Diallylacetal | 2.84 | — | | — | | AIBN 0.12 | Methanol 10 | 90 × 8 | 98 | C: 47.91 (47.86) H: 5.11 (5.06) O: 5.49 (5.54) Br: 41.49 (41.53) |
| 23 | 3-(1,2-dibromoethyl)styrene | 8.70 | Di(p-vinylphenyl)ether | 4.45 | — | | — | | AIBN 0.13 | Ethanol 10 | 90 × 8 | 96 | C: 56.62 (56.65) H: 4.48 (4.45) O: 2.46 (2.43) Br: 36.44 (36.47) |
| 24 | 3-(1,2-dibromoethyl)styrene | 8.70 | Diallyl terephthalate | 4.93 | — | | — | | AIBN 0.14 | Ethanol 10 | 90 × 8 | 99 | C: 51.19 (51.13) H: 4.32 (4.29) O: 9.31 (9.39) Br: 35.18 (35.19) |
| 25 | 4-(1,2-dibromoethyl)styrene | 8.70 | Ethylene glycol dimethacrylate | 3.96 | — | | Styrene | 1.04 | AIBN 0.14 | Ethanol 10 ml | 90 × 8 | 96 | C: 50.86 (50.83) H: 4.92 (4.85) O: 9.28 (9.34) Br: 34.94 (34.98) |
| 26 | 4-(1,2-dibromoethyl)styrene | 8.70 | — | | Trivinylbenzene | 3.12 | Ethylstyrene | 1.32 | AIBN 0.13 | Toluene 10 | 90 × 8 | 98 | C: 58.41 (58.47) H: 5.11 (5.06) Br: 36.48 (36.47) |
| 27 | 4-(1,2-dibromoethyl)styrene | 8.70 | Methylene bisacrylamide | 3.08 | — | | Styrene | 1.04 | AIBN 0.13 | Methanol 10 | 90 × 8 | 96 | C: 48.72 (48.70) H: 4.58 (4.56) N: 4.35 (4.37) O: 4.93 (4.99) Br: 37.42 (37.38) |
| 28 | 4-(1,2-dibromoethyl)styrene | 8.70 | Diallyl maleate | 3.92 | — | | — | | AIBN 0.13 | Methanol 10 | 90 × 8 | 98 | C: 47.62 (47.57) H: 4.35 (4.31) O: 10.11 (10.14) Br: 37.92 (37.98) |
| 29 | 4-(1,2-dibromoethyl)styrene | 8.70 | Divinylketone | 1.64 | — | | Styrene | 1.04 | AIBN 0.11 | Toluene 10 | 90 × 8 | 99 | C: 50.61 (50.65) H: 4.47 (4.43) O: 2.85 (2.81) Br: 42.07 (42.12) |
| 30 | 4-(1,2-dibromoethyl)styrene | 8.70 | — | | Triallyl citrate | 6.25 | — | | AIBN 0.15 | Methanol 10 | 90 × 8 | 97 | C: 48.21 (48.22) H: 4.78 (4.72) O: 14.92 (14.99) Br: 32.09 (32.08) |

EXAMPLE 31

Into a 1-liter four-neck flask equipped with a thermometer, reflux condenser, and stirrer were charged 2.0 g of commercial polyvinyl alcohol and 25 g of sodium chloride dissolved in 400 g of pure water. To the flask was further added with stirring a mixture composed of 30.0 g of 3-(1,2-dibromoethyl)styrene, 10.0 g of divinylbenzene (purity: 56%, m/p=7/3, containing 44% of ethylstyrene), 50.0 g of m-xylene, and 0.4 g of 2,2'-azobisisobutyronitril. Stirring was continued for 1 hour at 60° C., for 2 hours at 70° C., and for 4 hours at 80° C. After cooling and washing, there were obtained spherical particles 0.1 to 1.0 mm in diameter.

Thirty grams of the particles was placed in a 500-ml four-neck flask equipped with a thermometer, reflux condenser, and stirrer. To the flask was added 35.0 g of ethyl ester of iminodiacetic acid dissolved in 200 ml of ethanol. The reactants were stirred for 48 hours at 80° C. Then, 16.0 g of sodium hydroxide dissolved in 100 ml of pure water was added, followed by stirring for 5 hours at 90° C. After cooling and rinsing, the resulting particles underwent the following test to evaluate its ability to remove metal ions.

An aqueous solution containing 100 mg each of metal in 1 liter was prepared by dissolving a cupric chloride and ferric chloride in pure water. 5.0 g of the abovementioned particles was added to the solution, and after 24 hours, the metal ions remaining in the solution were determined. The content of Cu and Fe ions was less than 0.1 mg each.

EXAMPLE 32

Into a 50-ml ampoule were charged 10.0 g of 3-(1,2-dibromoethyl)styrene, 20 ml of propanol and 0.05 g of azabisisobutyronitrile. After complete mixing and dissolving, the air in the ampoule was replaced with nitrogen, and the ampoule was sealed. The ampoule was dipped in water at 90° C. for 24 hours to bring about reaction. After cooling, the ampoule was broken and the content was taken out and charged in a 300-ml four-neck flask equipped with a thermometer, reflux condenser, and stirrer. To the flask was further added 26.1 g of ethyl ester of iminodiacetic acid dissolved in 100 ml of ethanol. The reactants were stirred for 48 hours at 70° C. Then, 6.6 g of sodium hydroxide dissolved in 100 ml of pure water was added, followed by stirring for 5 hours at 90° C. After cooling and rinsing, and resulting particles were subjected to the same test as in Example 31 to evaluate its ability to remove metal ions, and the same results as in Example 31 were obtained.

EXAMPLE 33

8.20 g of 3-(1,2-dibromoethyl)styrene, 1.80 g of styrene, 10.0 g of m-xylene and 0.10 g of azobisisobutyronitril were uniformly mixed and charged in a 30-ml ampoule. Then the air in the ampoule was replaced with nitrogen, and the ampoule was sealed. The ampoule was dipped in water at 90° C. for 24 hours to bring about reaction. After cooling the ampoule was broken and the content was taken out.

The resulting polymer was charged in a 200-ml four-neck flask equipped with a thermometer, reflux condenser, and stirrer. To the flask was added 12.0 g of ethyl ester of iminodiacetic acid dissolved in 100 ml of ethanol. The reactants were stirred for 48 hours at 70° C. Then, 4.0 g of sodium hydroxide dissolved in 50 ml of pure water was added, followed by stirring for 5 hours at 90° C. After cooling and rinsing, the resulting particles were subjected to the same test as in Example 31 to evaluate its ability to remove metal ions, and the same results as in Example 31 were obtained.

While the invention has been described in detail and with reference to specific embodiments thereof, it will be apparent to one skilled in the art that various changes and modifications can be made therein without departing from the spirit and scope thereof.

What is claimed is:

1. A linear or crosslinked polymer comprising 10 to 100 mol% of the polymeric units represented by the structural formula (2), 0 to 50 mol% of polymeric units represented by the structural formula (3) and/or (4), and 0 to 90 mol% of polymeric unit represented by the formula (5):

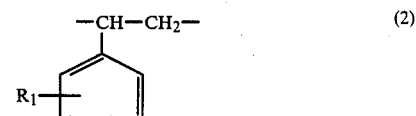

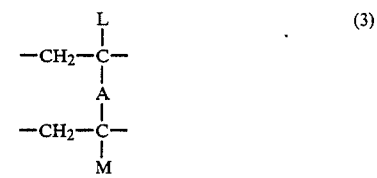

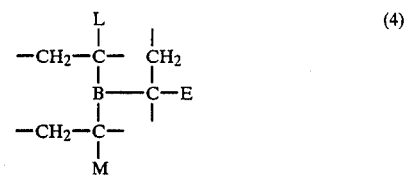

wherein $R_1$ represents a hydrogen atom and a hydrocarbon group containing 1 to 10 carbon atoms; $X_1$ and $X_2$ are halogen atoms; L, M, and E represent hydrogen atoms and a methyl group; A is selected from the group consisting of (i)

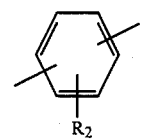

wherein $R_2$ is a hydrogen atom or a hydrocarbon group containing 1 to 5 carbon atoms, (ii)

(iii)

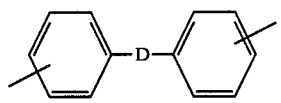

wherein D represents —O—, —S—, —NH—, or an alkylene group containing 1 to 5 carbon atoms, (iv) —SO—, —CO—, or

(v) —CH$_2$—NH—CH$_2$—,
(vi)

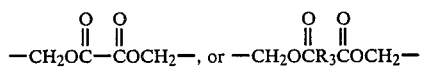

wherein R$_3$ is a divalent hydrocarbon group containing 1 to 8 carbon atoms, (vii)

wherein R$_4$ is a divalent hydrocarbon group containing 1 to 5 carbon atoms, and (viii)

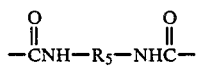

wherein R$_5$ is a divalent hydrocarbon group containing 1 to 3 carbon atoms; and B is selected from the group consisting of (i)

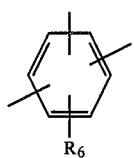

wherein R$_6$ is a hydrogen atom or a hydrocarbon group containing 1 to 5 carbon atoms, (ii)

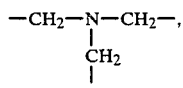

and
(iii)

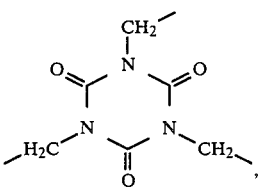

and P and Q each represents a hydrogen atom, a halogen atom, an alkyl or haloalkyl group containing 1 to 10 carbon atoms, a cyano group, an aryl group, a halogenophenyl group, a hydroxyphenyl group, a hydroxymethylphenyl group, a carboxyphenyl group, an alkylphenyl group containing an alkyl moiety of 1 to 5 carbon atoms, a haloalkylphenyl group, a hydroxyalkylphenyl group, a hydroxymethylalkylphenyl group, a carboxyalkylphenyl group, COOR$_7$ wherein R$_7$ is a hydrogen atom or a hydrocarbon group containing 1 to 10 carbon atoms, COR$_8$ wherein R$_8$ is a hydrogen atom or a hydrocarbon group containing 1 to 10 carbon atoms, OCOR$_9$ wherein R$_9$ is a hydrocarbon group containing 1 to 10 carbon atoms, and CONHR$_{10}$ wherein R$_{10}$ is a hydrogen atom or a hydrocarbon group containing 1 to 10 carbon atoms.

2. A polymer as claimed in claim 1, wherein R$_1$ represents a hydrogen atom, a methyl group and an ethyl group.

3. A polymer as claimed in claim 1, wherein X$_1$ and X$_2$ each represents a chlorine atom, a bromine atom and an iodine atom.

4. A polymer as claimed in claim 1, wherein X$_1$ and X$_2$ are bromine atoms.

5. A polymer as claimed in claim 1, wherein L, M, and E are hydrogen atoms.

6. A polymer as claimed in claim 1, wherein A is

7. A polymer as claimed in claim 1, wherein B is

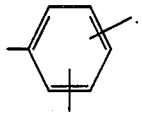

8. A polymer as claimed in claim 1, wherein one of P and Q is a hydrogen atom.

9. A polymer as claimed in claim 1 wherein said polymer is composed of the polymeric unit represented by the structural formula (2) and has a molecular weight of 1,000 to 1,000,000.

10. A polymer as claimed in claim 9, wherein R$_1$ represents a hydrogen atom, a methyl and an ethyl group.

11. A polymer as claimed in claim 9, wherein X$_1$ and X$_2$ each represents a chlorine atom, a bromine and an iodine atom.

12. A polymer as claimed in claim 9, wherein $X_1$ and $X_2$ are bromine atoms.

13. A polymer as claimed in claim 1 wherein said polymer is composed of the polymeric units represented by the structural formulas (2) and (5), the content of the polymeric units (2) being 10 to 98 mol%, and said polymer having a molecular weight of 1,000 to 2,000,000.

14. A polymer as claimed in claim 13, wherein $R_1$ represents a hydrogen atom, a methyl group and an ethyl group.

15. A linear copolymer as claimed in claim 13, wherein $X_1$ and $X_2$ each represents a chlorine atom, a bromine atom and an iodine atom.

16. A polymer as claimed in claim 13, wherein $X_1$ and $X_2$ are bromine atoms.

17. A polymer as claimed in claim 13, wherein one of P and Q is a hydrogen atom.

18. A polymer as claimed in claim 1 wherein said polymer is composed of 10 to 98 mol% of the polymeric unit represented by the structural formula (2), 2 to 50 mol% of the polymeric unit represented by the structural formula (3) and/or (4), and 0 to 80 mol% of polymeric unit represented by the structural formula (5).

19. A polymer as claimed in claim 18, wherein $R_1$ represents a hydrogen atom, a methyl and an ethyl group.

20. A polymer as claimed in claim 18, wherein $X_1$ and $X_2$ each represents a chlorine atom, a bromine atom and an iodine atom.

21. A polymer as claimed in claim 18, wherein $X_1$ and $X_2$ are bromine atoms.

22. A polymer as claimed in claim 18, wherein L, M, and E are hydrogen atoms.

23. A polymer as claimed in claim 18, wherein A is

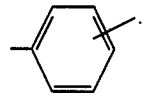

24. A polymer as claimed in claim 18, wherein B is

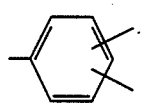

25. A polymer as claimed in claim 18, wherein one of P and Q is a hydrogen atom.

* * * * *